United States Patent [19]

Koepnick

[11] Patent Number: 5,690,657

[45] Date of Patent: *Nov. 25, 1997

[54] UNIVERSAL AUTOMATED KERATECTOMY APPARATUS AND METHOD

[76] Inventor: Russell G. Koepnick, 4435 N. 78th St. #113A, Scottsdale, Ariz. 85251

[*] Notice: The term of this patent shall not extend beyond the expiration date of Pat. No. 5,496,339.

[21] Appl. No.: 441,789

[22] Filed: May 16, 1995

Related U.S. Application Data

[63] Continuation-in-part of Ser. No. 245,228, May 17, 1994, Pat. No. 5,496,339.
[51] Int. Cl.[6] .................................. A61B 17/32
[52] U.S. Cl. .................................. 606/166
[58] Field of Search .................... 606/1, 108, 166, 606/167

[56] References Cited

U.S. PATENT DOCUMENTS 4,662,370  5/1987  Hoffmann et al. .
5,133,726  7/1992  Ruiz et al. .
5,496,339  3/1996  Koepnick .

Primary Examiner—William Lewis
Attorney, Agent, or Firm—James Creighton Wray

[57] ABSTRACT

A surgical device for altering the curvature of an eye includes a base which carries a transparent insert, a drive device, a knife edge coupled to the drive device and movable to a plane immediately adjacent the under surface of the transparent insert. The transparent insert includes a face having a surface portion shaped according to a predetermined correction. The base further includes a suction ring which forms a vacuum chamber with the eye. The suction ring is placed against the eye. Application of vacuum results in the cornea of the eye being urged into engagement with the shaped surface portion. Actuation of the drive device moves the knife edge whereby the cornea is cut. Only the knife edge traverses the insert.

38 Claims, 4 Drawing Sheets

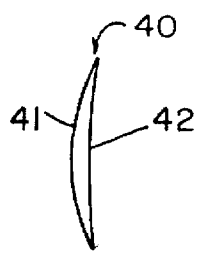
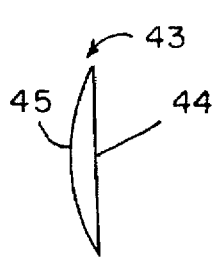
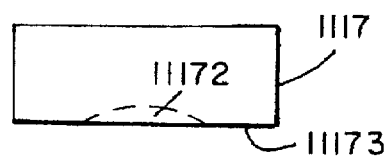
FIG. 1  FIG. 2  FIG. 3
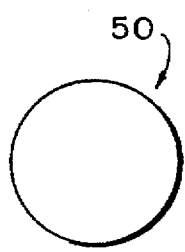
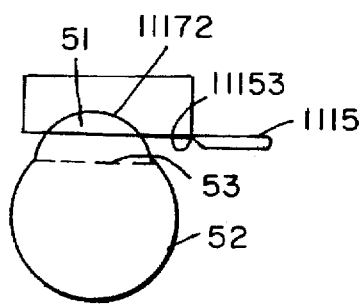
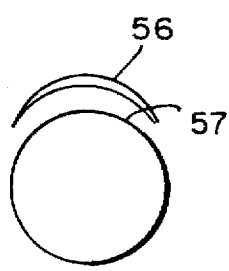
FIG. 4  FIG. 5  FIG. 6
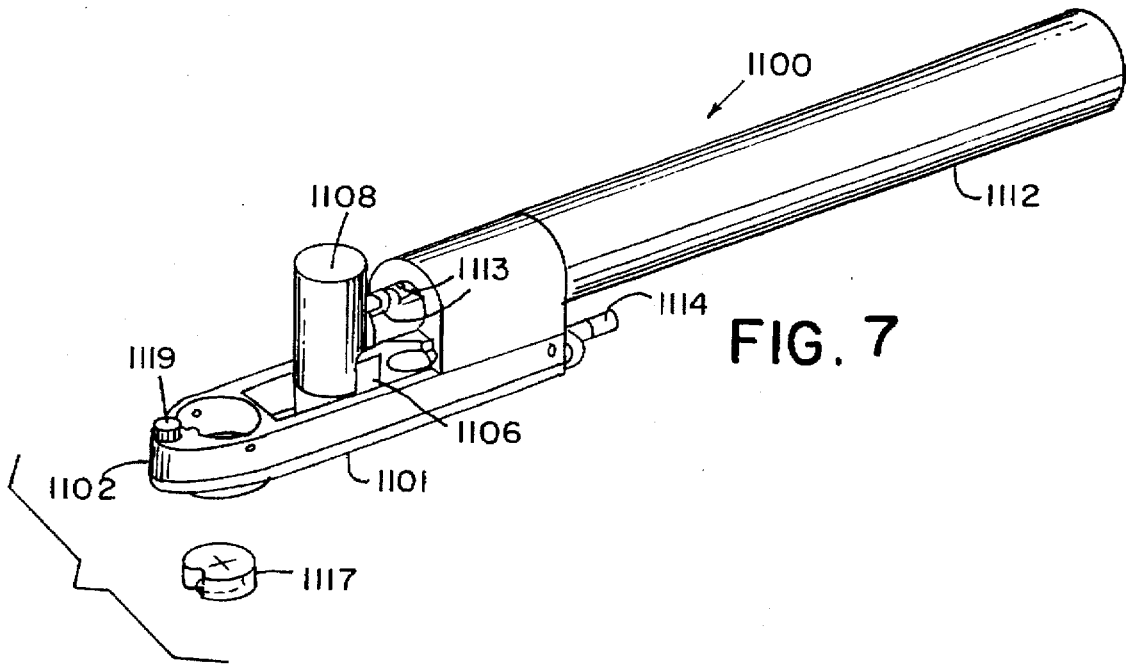
FIG. 7

UNIVERSAL AUTOMATED KERATECTOMY APPARATUS AND METHOD

RELATED APPLICATIONS

This is a continuation-in-part of U.S. patent application Ser. No. 08/245,228 filed May 17, 1994 for Universal Keratectomy Apparatus and Method, now U.S. Pat. No. 5,496,339.

BACKGROUND OF THE INVENTION

This invention relates generally to apparatus and methods for mechanically performing single or multiple pass keratectomy for the correction of eye abnormalities including myopia, hyperopia and astigmatism, and relates more particularly to a surgical device that slices a corneal disk from the eye with a reciprocating knife which is advanced over the eye.

One of the first procedures for refractive surgery was the Barraquer microkeratome which placed against the cornea a flat applanate surface supported with the knife (as in a plane) guided by spaced apart dovetailed guides which formed rails on a suction ring applied to the sclera and then manually passed across the cornea at an angle thereto a power driven reciprocating knife edge in a guideway to remove a round lamellar (sides parallel to the surface of the cornea) disk. The thickness of the cut disk was controlled by the thickness of a spacer plate (numerous plates for various thicknesses) and the cut disk rolled up into a groove between the spacer plate and the block carrying the knife as the cut was made. The cut disk was then frozen, lathed and replaced. The procedure was known as keratomileusis.

Mechanical devices known as keratomes have been utilized to perform multiple lamellar cuts of the cornea. In this procedure, a first disk is cut. Then a second smaller disk is cut and removed. The first disk is sewn back on. This procedure, known as keratomileusis in-situ, eliminated the freezing process and overcame many of the problems of the keratomileusis procedure. However, keratomes still lacked precision, predictability and the ability to make smooth corneal cuts.

Microkeratomes, for example, Giraud et al U.S. Pat. No. 5,288,292, applicant being a co-inventor thereof, have replaced Barraquer's multiple spacer plates for controlling the thickness of the cut with a single adjustable plate which controls the space between the plate and knife edge and, hence, the slice thickness. Micrometers have been placed on the microkeratome to precisely control the thickness.

The procedure known as radial keratotomy is used extensively for the correction of low to medium myopia and astigmatism. The procedure involves changing the shape of the cornea by making deep corneal cuts which are 80–90% of corneal thickness extending out from a central optical zone of about 3 mm. diameter. While many patients report satisfactory results, others are bothered by regression and many experience a starburst effect from the reflection of light at nighttime when the pupil is dilated larger than 3 mm. The scars from the deep corneal incisions scatter light at night time. Radial keratotomy is usually limited to about 8 diopters of refractive correction.

Eximer lasers have been used for corneal sculpturing for correction of myopia and astigmatism. The eximer laser ablates (removes by vaporization) the cornea in a manner that results in removing a lenticular (sides not parallel to the surface of the cornea) disk from the cornea with a diameter of about 5–6 mm. The procedure requires that the epithelium (thin outer layer of the eye) be scrapped off. Then the eximer laser ablates the cornea in a series of stepped ablations which leave a less than smooth surface on the corneal bed. The procedure subjects patients to substantial pain for a few days and obstructed vision for months. The use of eximer lasers to remove superficial irregularities of the cornea has met with mixed success due to ablation induced hyperopic shifts of corneal refraction.

U.S. Pat. No. 4,662,370 shows a device in which the adjustable movable plate of the earlier devices has been replaced by a fixed plate. This device begins the cut of the cornea outside of the correction zone, passing superstructure over the cornea blocking the surgeons view during the cut, and requires the complexity and cost of multiple vacuums chambers.

There remains a long felt need for a smooth cutting keratome that can be used for all defective vision corrections including those requiring irregular cuts, cuts only under a prescribed, predetermined corrected surface, provides automated advance without blocking the surgeon's vision during the cut.

SUMMARY OF THE INVENTION

A surgical device in accordance with the principles of the invention alters the curvature of an eye by cutting a corneal disk with a knife edge which is advanced under a transparent member or insert which has a surface portion adjacent the plane of movement of said knife edge shaped according to a predetermined prescriptive correction. The device is configured such that only the knife traverses the eye so that the surgeon can observe cutting by the knife through the transparent insert during the entire procedure. Further in accordance with the principles of the invention, the knife edge is reciprocated from side to side at high speed to facilitate the smooth cutting of the tissue. More specifically, the knife is pinned at one end such that the knife edge positioned at the opposite end swings from side to side in an arc at high speed.

The device includes a suction ring which is positioned and held against the sclera of the eye with the corrected surface portion of the transparent member touching the cornea of the eye. Further in accordance with the invention the suction ring device and a sclera of an eye when received therein form the single and sole annular vacuum chamber in the entire assembly.

The transparent member is easily replaceable as an insert and has a visible crosshair image for aligning the insert with the cornea prior to cutting. The insert is keyed such that it can be placed in the device in an exact and precise alignment.

The invention has many advantages over other mechanical keratomes, eximer lasers and radial keratectomy. One major advantage is that surgery utilizing the device is reversible. Reversibility can be accomplished by simply replacing the excised corneal disk or by excising another disk from a donor cornea using the same insert as used for the original operation. An additional advantage is that highly accurate prescriptive corrective cuts can be made.

BRIEF DESCRIPTION OF THE DRAWINGS

The invention will be better understood from a reading of the following detailed descriptions of embodiments of the invention taken in conjunction with the drawings in which:

FIG. 1 is a schematic section of a lenticular corneal disk cut;

FIG. 2 is the optical equivalent of FIG. 1 in planoconvex form;

FIG. 3 is a transparent insert of the present invention with a concave prescriptive correction formed into its bottom surface;

FIG. 4 is a schematic of the cornea of an eye before vacuum is applied;

FIG. 5 is a schematic of the cornea with the vacuum applied;

FIG. 6 is a schematic of the cornea after the cut with the vacuum off;

FIG. 7 is an isometric view of an embodiment of the invention with an insert shown below;

DETAILED DESCRIPTION

Figure 8:
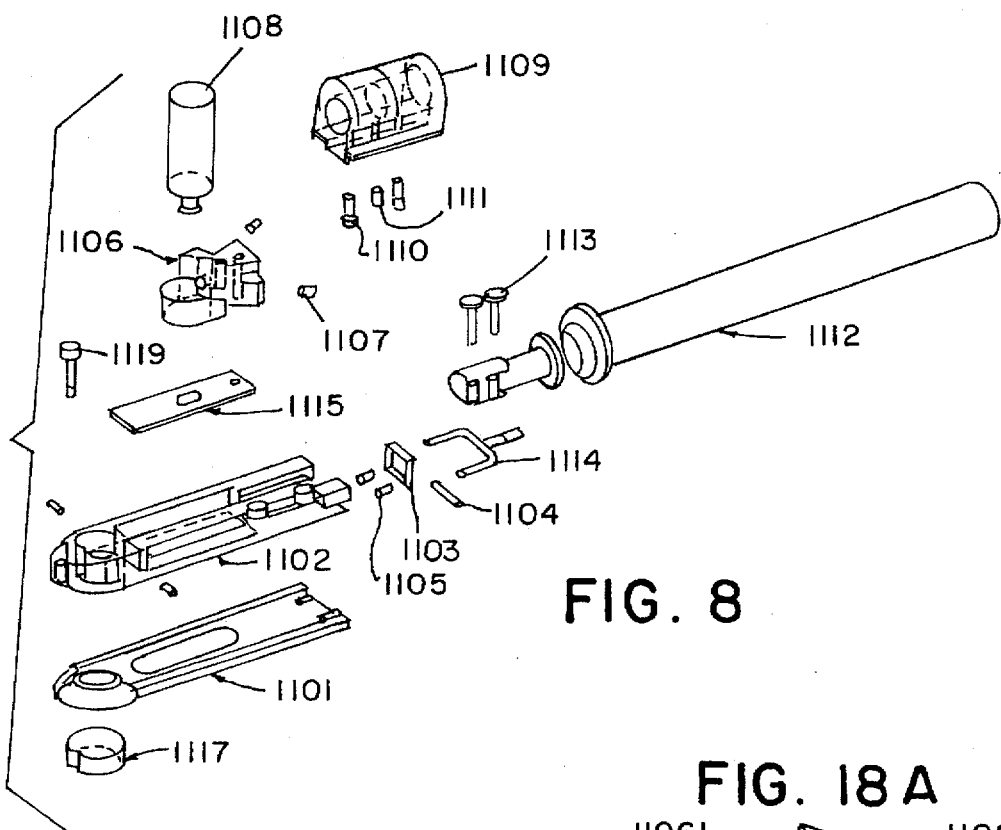
FIG. 8 is an exploded assembly drawing of the embodiment of FIG. 7 illustrating is schematic form each of the components forming the second embodiment.

The change in the corneal surface using the surgical device of the present invention will be determined by an optical correction formed into a custom made member or insert based upon a doctor's prescription. The prescription is similar to the prescription a doctor might give to an optical laboratory for the purpose of grinding lenses for eye glasses or for contact lenses.

FIG. 1 illustrates a particular prescribed corrective portion which is to be removed from a patient's eye. This lenticular cut portion 40 which is to be removed from an eye has two surfaces 41, 42 which form a positive meniscus (crescent) in shape. This prescriptive correction is mathematically converted to the optical equivalent 43 seen in FIG. 2. Equivalent 43 has a planar side 44 and a convex side 45. In accordance with the invention, the optical prescription is sculpted into a flat face 11173 of an insert 1117 shown in FIG. 3. The insert 1117 is then inserted into applicant's instrument 1100. The instrument is placed against the eye such that the eye is in contact with the insert. A knife edge is moved under the insert and an equivalent cornea portion of the eye is cut off thereby altering the curvature of the cornea by precisely the prescribed amount. The prescriptive member or insert 1117 as shown in FIG. 3, has surface 11173 profiled to correspond to the plano convex shape of FIG. 2. As shown in FIG. 3, corrective portion 11172 of the insert 1117 corresponds to the equivalent shape 43.

The insert 1117 is carried by a device 1100 shown in its entirety in FIG. 7 and which is described in greater detail below. The device 1100 serves to hold the insert 1117 in position on an eye while a knife blade is passed under the insert and immediately adjacent thereto. In accordance with the invention a vacuum chamber is formed by a suction ring carried by the device 1100 and the eye adjacent to the lower surface of the insert 1117. Application of partial vacuum to this chamber raises the innerocular pressure of the eye causing the cornea of the eye to be urged into contact with the prescriptive portion of the insert 1117.

FIGS. 4, 5, and 6 illustrate the sequence of operation on an eye 50 in schematic form. The eye 50 is shown schematically without the device of the present invention in FIG. 4. In FIG. 5 the surgical device 1100 which is not shown is placed into contact with the eye and a partial vacuum is applied to the sclera 52. The vacuum is adjusted to a level such that forces are applied to the cornea 51 by the suction ring raising the innerocular pressure in the eye 50 and forcing the eye to bulge outwardly causing the cornea 51 to fill the prescriptive concave depression 11172 of the insert 1117. The portion of cornea 51 filling the depression 11172 in the insert 1117 is rapidly but smoothly excised by a knife 1115 oscillating from side to side. Knife 1115 is advanced across the eye at a predetermined rate in a plane parallel and adjacent to the flat face 11173 of the insert 1117. The knife 1115 has a knife edge which is flat on its upper surface and beveled on its lower surface 11153.

After the cut has been made, the partial vacuum is released. As shown schematically in FIG. 6, when the vacuum is released the cornea 51 will return to its normal shape less the disk portion 56 excised by the cut. The disk 56 is of a lenticular cut of the required refraction so that the remaining cornea 57 has precisely the proper refractive power for emmetropia (normal vision).

All the components to assemble the device 1100 are shown in FIG. 7 and the exploded assembly drawing of FIG. 8. As shown in FIGS. 7 and 8, device 1100 includes a single piece body 1102. Body 1102 carries a pin registration plate 1103. The plate 1103 has two registration pins 1105 which are press fit into apertures in the plate 1103. Plate 1103 is retained on base 1102 by means of a locking pin 1104 which is pressed into corresponding apertures in plate 1103 and body 1102.

A suction plate 1101 is assembled to the body 1102 at one end by means of two apertures which engage the pins 1105. At the other end, the suction plate is retained on the body by means of a retaining screw 1119 which extends through the body 1102. Captured between the suction plate 1101 and the body 1102 is the optical insert 1117 and a knife 1115. The knife 1115 and the insert 1117 are for purposes of clarity not shown in 29 in the actual positional relationship relative to the body 1102 and the plate 1101. An actuator holder 1109 is fastened to the base 1102 by means of screw fasteners 1110. A linear actuator 1112 is captured in and supported in the holder 1109. A set screw 1111 is used to secure the actuator in position. The suction plate includes through bores which are in communication with apertures in the vicinity of the suction ring to form a suction chamber. The through bores exit the rear of the suction plate and are connected to a vacuum source by, for example, a vacuum manifold 1114.

The actuator 1112 has a piston 11121 extending from its one end. A motor holder 1106 is secured to the piston 11121 by means of fasteners 1107. The motor holder 1106 carries a blade drive motor 1108. The motor holder also carries the knife 1115 on its bottom surface.

The linear actuator 1112 serves to advance the knife 1115 such that knife 1115 traverse the area of the suction ring plate 1111 which carries the suction ring. While the knife 1115 is advanced, the blade motor 1108 drives the knife 11115 such that the leading edge of the knife oscillates from side to side.

Figure 9:
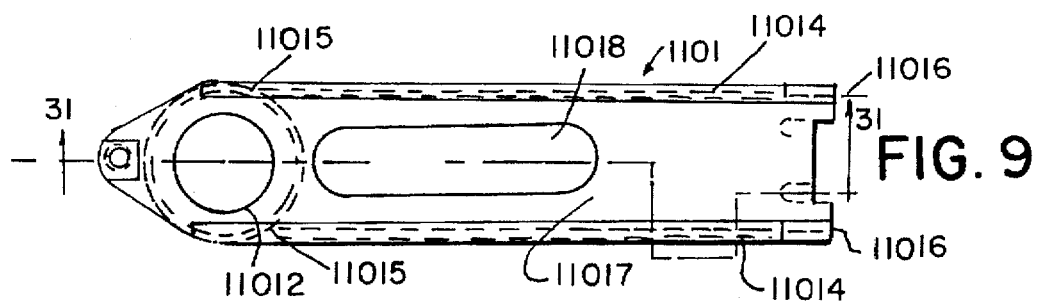
FIG. 9 is a top view of a suction plate.
Figure 10:
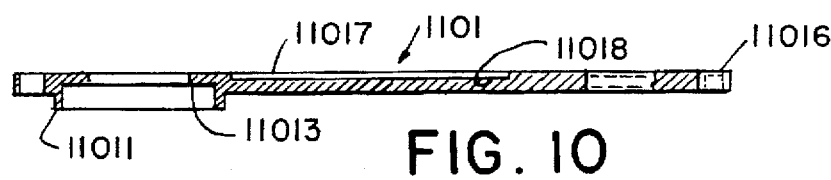
FIG. 10 is a side view of the plate of FIG. 9 taken in cross section along lines 9—9.
Figure 11:
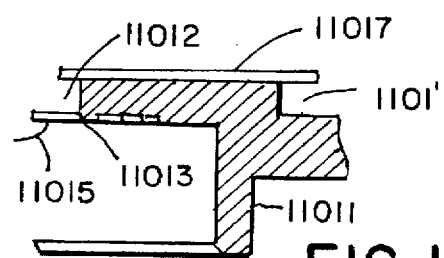
FIG. 11 is a detail of the circled portion of FIG. 10.

Turning now to FIGS. 9, 10 and 11, the suction ring plate 1101 includes a suction ring 11011. Suction ring 11011 has a stepped portion produced by an inner aperture 11012 in the plate 1101. A square corner or shoulder 11013 is formed which will exert a force against the sclera of an eye. This force in conjunction with the forces exerted by the peripheral edge of suction ring 11011 against the eye will cause the eye to generate equilibrium forces which urge the eye into contact with the insert 1117. The aperture 11012 has a diameter which is smaller than the diameter of the prescriptive insert 1117 which is positioned above the aperture 11012. The plate 1101 includes two through bores 11014. Bores 11014 have one end which opens into the interior of the suction ring 1101 at openings 11015 and at the other end each has a port 11016 which receives the vacuum manifold 1114. As shown in FIG. 11, beveled edges are used at the edges of the suction ring 11011 and shoulder 11013. The suction plate includes a recess 11017 in its top surface. The recess 11017 is sized to receive the knife 1115 and to retain the knife in planar position such that it may be moved forward and back in reciprocating movement within the plane immediately above the suction ring 11011 and immediately below the insert 1117. The recess is of a width such that the knife 1115 may also pivot from side to side within the same plane as the reciprocating movement. A second recess 1108 is provided which allows the pivot pin 11061 which extends downward from the motor holder 1106 to freely slide back and forth as the knife 1115 is advanced and retracted.

Figure 12:
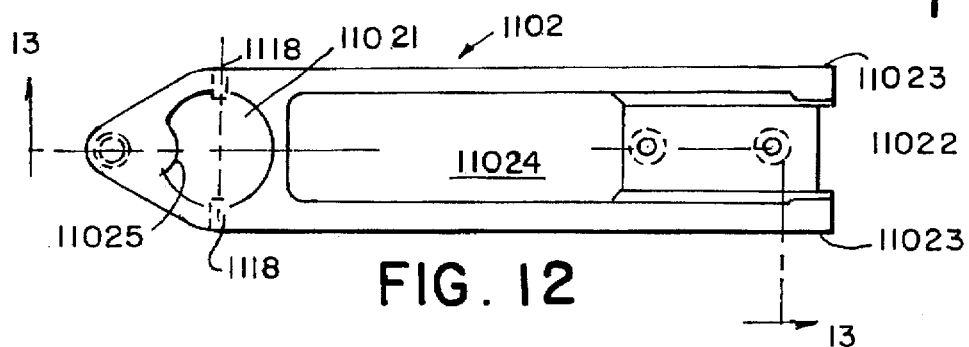
FIG. 12 is a top view of the body member.
Figure 13:
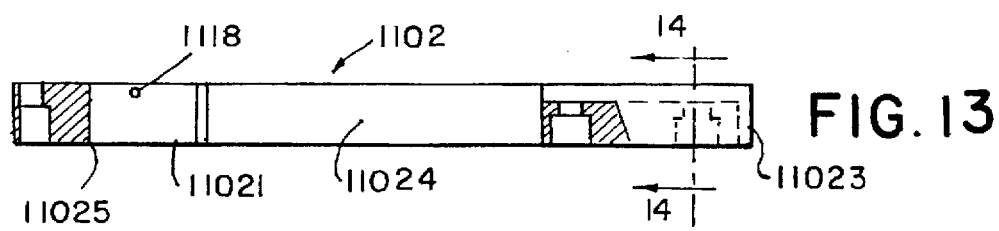
FIG. 13 is a side view of the body member of FIG. 12 taken in partial cross section along lines 13—13.
Figure 14:
FIG. 14 is a cross section view of the body member taken along lines 14—14 in FIG. 13.
Figure 24:
FIG. 24 illustrates a stainless steel knife which has been backstropped.
Figure 23:
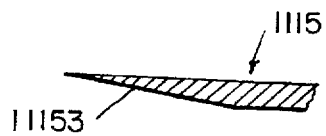
FIG. 23 is an enlarged view of the edge of the knife of FIG. 22.

The one piece body assembly 1102 is shown in detail in FIGS. 12, 13 and 14. The body 1102 includes an insert receiving aperture 11021. The rear portion of the body 1102 includes a recess 11022 which receives the pin registration plate 1103. The recess is sized such that the plate 1103 is firmly held in place. A pin 1104 is inserted through apertures 11023 to retain the plate 1103. The plate 1103 has two registration pins 1105 which are received in corresponding apertures in the suction plate 1101. The other end of the suction plate 1101 is removeably retained against the bottom of the body 1102 by means of screw 1119 which is received in bore 11023. Body 1102 has a central aperture 11024 in which the motor holder 1106 and the blade drive motor 1108 may reciprocate back and forth. The body 1102 includes apertures 11024 which receive screws that fasten the actuator holder 1109 to the body 1102.

Prior to assembling the suction plate 1101 to the body 1102, the prescriptive insert 1117 is slid into the aperture 11021. Stop pins 1118 carried in the body 1102 limit the movement of the insert 1117 in the upward axial direction. When the suction plate 1101 is coupled to the base 1102, the suction plate 1101 prevents movement of the insert 1117 in the axial downward direction. Thus the insert 1117 is captured in the body 1102. It should be noted that although stop pins are utilized in this embodiment, the through bore aperture 11021 could be stepped to provide a shoulder against which the upper surface of the insert 1117 rests. In addition, the knife 1115 is captured between the body 1102 and the suction plate 1101.

Figure 15:
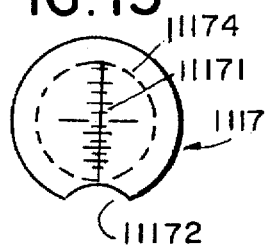
FIG. 15 is a top view of an insert used in the device of FIG. 7.
Figure 16:
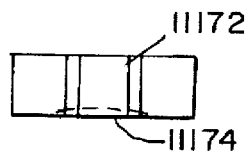
FIG. 16 is a side view of the insert of FIG. 15.
Figure 17:
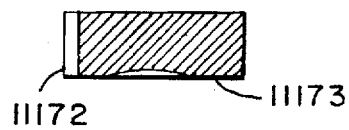
FIG. 17 is a cross section view of the insert taken along lines 38—38 in FIG. 16.

The insert is shown in FIGS. 15, 16 and 17. The insert 1117 of this embodiment includes an alignment scale 11171 which is laser etched into its upper surface, along with cross hairs. A keyway 11172 integrally formed in the insert 1117 engages a corresponding lug 11025 on the body 1102 to provide precise registration of the insert 1117 in the device 1100. Alternatively, the keyway or groove 11172 may extend axially only over a portion of the insert rather than along its entire length. In this alternate instance, the lug would be no longer than the keyway or groove and could be a pin rather than a lug.

Figure 18:
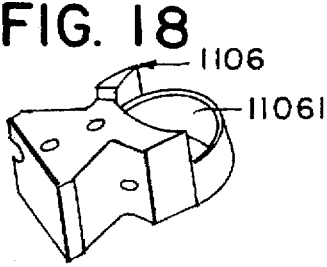
FIGS. 18 and 18a show the motor holder in right and left side isometric views.
Figure 18A:
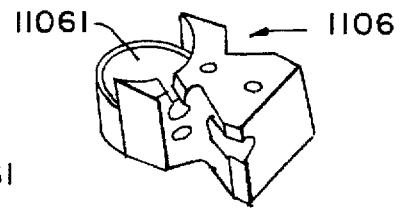
Figure 19:
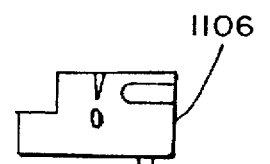
FIG. 19 illustrates the motor holder inside view.

The motor holder is shown in FIGS. 18, 18a, and 19. Motor holder 1106 includes a motor receiving ring 11061 to receive the blade motor 1108.

A linear actuator 1112 is secured to the device 1100 by utilizing the actuator holder 1109. The linear actuator is a commercially available device and includes a piston 11121 which extends from the actuator 1112 and which is coupled to the motor holder 1106 by fasteners 1113.

Figure 20:
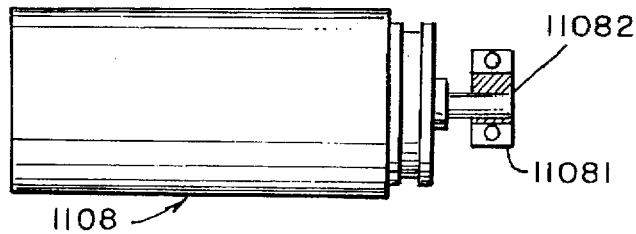
FIG. 20 is a side view of the knife motor.
Figure 21:
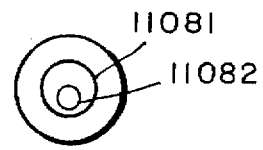
FIG. 21 is an end view of the eccentric bearing shown in FIG. 24.

The knife motor 1108 is shown in FIGS. 20 and 21. The shaft 11082 of the motor 1108 terminates in eccentric 11081 which engages the aperture 11152 of the knife 1115. The eccentric is formed by a bearing 11082 on shaft 11081. The bearing 11082 is pressed onto the shaft 11081 such that it is off center to form an eccentric. Alternatively the shaft 11081 could have its end machined into an eccentric. With the rear end of the knife pinned to the holder 1106 by pivot pin 11061, the rotation of the eccentric in the slot 11152 in the knife 1115 will cause the front edge of the knife 1115 to swing from side to side in an arc.

The knife 1115 is shown in detail in FIGS. 20 and 21. The knife includes a pivot hole 11151 which engages a pivot pin 11061 of the motor holder 1106. The knife also includes aperture 11152 which receives eccentric 11081 on the output shaft 11082 of motor 1108. The aperture or slot 11152 is of a width corresponding to the diameter of the eccentric 11081 and a length which is at least twice the distance of the center of the eccentric to its furthest point. By utilizing an eccentric 11081 in conjunction with a pivot pin, as the motor shaft 11082 turns, the knife 1115 will swing side to side through an arc to enhance cutting as the knife is reciprocally advanced.

Figure 22:
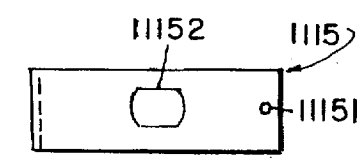
FIG. 22 is a top planar view of a knife.

It has been found that the knife 1115 is ideally formed of zirconium. Zirconium is particularly advantageous because with zirconium, an extremely smooth and flat upper surface may be obtained on the knife 1115. With zirconium the top of the cutting edge may be made flat and the bottom surface 11151 may be beveled so that a chisel edge is found to achieve extremely smooth cuts. In contrast, with stainless steel, as the knife is sharpened a wire is formed along the cutting edge. This wire may be eliminated by back stropping of the edge. However, after backstropping, the top edge of the knife will be concave as shown in FIG. 22. With the top edge concave, cuts of the cornea will not have the prescriptive accuracy desired.

Operation of the device is simple. The physician places a custom made insert such as insert 1117 into the cutting instrument 1100. The physician then places the instrument 1100 over the patient's eye with the insert 1117, which is made of a clear material, over the cornea. The physician centers the insert on the eye and activates a vacuum source so that the suction size will retain the eye in position relative to the insert. The physician then activates knife motor 1108, and activates the linear actuator 1112 which automatically advances the knife a preset distance at a predetermined speed which is approximately 0.5 to 1.0 mm/sec. When the knife advances to the preset point, the knife motor 1108 and linear actuator 1112 are automatically turned off and the partial vacuum is released. The entire procedure from centering of the optical zone to the completion of the cut should take no more than 30 seconds. A patch is placed over the patient's eye and the operation is complete.

With the present invention, highly precise corrections may be made because highly precise sculpting or grinding apparatus are commercially available to form the prescriptive corrective recess in the inserts. These apparatus in combination with computer technology allow forming the recess 11172 of the insert 1117 to exactness within two tenths of a micron.

Visual positional alignment is achieved using crosshairs 11171 as shown in FIG. 15 which allows the surgeon to look through the insert to align the crosshairs 11171 with the optical center of the eye after which the vacuum is applied. Insert 1117 is transparent and is preferably made of an acrylic plastic such as the well known PMMA. Equivalent materials include materials used for the manufacture of eye glasses or hard contact lens.

The insert 1117 may be alternatively provided with a convex, planar or irregular correction formed into the flat face 11173 of the insert 1117 to provide corresponding corrective cuts in the cornea.

Figure 26:
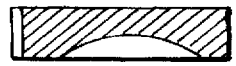
FIG. 26 illustrates an insert having an irregular correction formed therein.

Irregular corrections for such defects as astigmatism may be formed into the insert 1117 by means of a laser or by use of optical grinding machines. The resulting insert is shown in FIG. 26. Thus, the refractive correction for any degree of myopia, hyperopia, or astigmatism can therefore be precisely and predictably formed into an insert.

Figure 30:
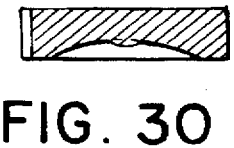
FIG. 30 illustrates an insert providing two prescriptive corrections.
Figure 28:
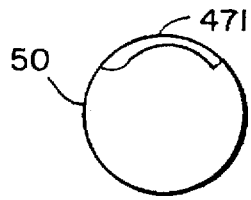
FIG. 28 illustrates the resulting cut on an eye from using the insert of FIG. 27.
Figure 27:
FIG. 27 illustrates an insert which produces a negative meniscus to correct for hyperopia.
Figure 29:
FIG. 29 illustrates an insert for producing a lamellar cut.
Figure 25:
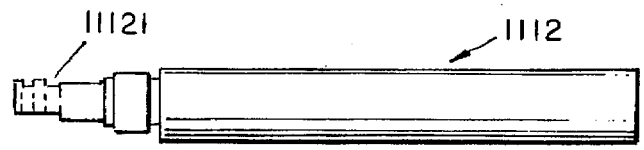
FIG. 25 shows the linear actuator.

FIG. 27 illustrates a negative meniscus cut which will correct for hyperopia and the resulting cut 471 which is produced in an eye 50 is shown in FIG. 28. FIG. 29 illustrates an insert which will produce a lamellar cut. FIG. 30 illustrates how an insert which provides multifocal corrections may be shaped.

The foregoing description of a preferred embodiment has been presented for the purposes of illustration and description. Many modifications and variations may be made without departing from the spirit or scope of the invention. It is intended that the scope of the invention be limited by the claims appended hereto.

What is claimed:

1. A surgical device for making a surgical cut to the cornea of an eye, said device comprising:

a base;

a single vacuum chamber adapted to engage the sclera of an eye, said vacuum chamber being connectable to a vacuum source;

an insert, said insert being carried on said base, said insert having a face disposed toward said eye, said face having a surface portion shaped according to a predetermined prescriptive correction, said insert being positioned such that said vacuum chamber is disposed adjacent said insert, and whereby application of vacuum to said vacuum chamber causes the cornea of said eye to engage said surface portion;

a knife provided on said base and movable in a plane transverse to said face and adjacent to said face, said knife having a cutting edge;

said base, said vacuum chamber and said insert being cooperatively shaped such that when said knife is moved in said plane, said knife will cut only corneal tissue of said eye in said plane;

a first drive apparatus drivingly connected to said knife for causing the cutting edge of said knife to swing from side to side in an arc in said plane;

a drive device coupled to said knife for moving said knife in reciprocal fashion in said plane to advance said knife to cut said cornea; and said drive device and said first knife apparatus positioned and operable such that only said knife is movable across said insert.

2. A surgical device in accordance with claim 1, wherein:
   said first drive apparatus comprises a motor having a drive shaft, said motor being positioned such that said drive shaft is substantially perpendicular to said plane.

3. A surgical device in accordance with claim 2, wherein:
   said first drive apparatus further comprises an eccentric carried by said drive shaft and coupled to said knife.

4. A surgical device in accordance with claim 3, wherein:
   said first drive apparatus further comprises a pivot connection to said knife adjacent said knife's other end.

5. A surgical device in accordance with claim 4, wherein:
   said knife includes a first aperture adapted to receive a pivot pin, and a second aperture adapted to receive said eccentric and sized such that rotation of said eccentric in said second aperture results in said knife swing in a side to side arc around an axis through said pivot pin.

6. A surgical device in accordance with claim 2, wherein:
   said drive device includes a shaft which is axially movable parallel to said plane; and
   said shaft is coupled to said first drive apparatus, whereby axial movement of said shaft results in movement of said knife in said plane.

7. A surgical device in accordance with claim 6, wherein:
   said drive device comprises a linear actuator.

8. A surgical device in accordance with claim 7, wherein:
   said first drive apparatus comprises a variable speed motor.

9. A surgical device in accordance with claim 1 wherein:
   said insert is transparent.

10. A surgical device in accordance with claim 2 wherein:
    said insert includes a crosshair image disposed in alignment with said shaped surface for aligning said insert with said eye prior to cutting.

11. A surgical device in accordance with claim 3 wherein:
    said crosshair includes scale markings.

12. A surgical device in accordance with claim 1 wherein:
    said vacuum chamber comprises a suction ring couplable to said vacuum source.

13. A surgical device in accordance with claim 13 wherein:
    said vacuum source will raise the inner ocular pressure in said eye forcing the cornea of said eye against said shaped surface portion.

14. A surgical device in accordance with claim 1 wherein:

said base includes a portion for receiving said insert and retaining said insert in registered alignment with said base.

15. A surgical device in accordance with claim 14 wherein:

said insert is transparent.

16. A surgical device in accordance with claim 15 wherein:

said insert includes scale markings thereon for aligning said insert over said eye.

17. A surgical device in accordance with claim 1 wherein:

said knife has its cutting edge shaped such that the top surface of said knife edge is flat and the bottom surface of said knife edge is beveled.

18. A surgical device comprising:

a base having a knife receiving recess;

a suction ring carried on said base and adapted to engage the sclera of an eye to form a single vacuum chamber with said eye;

an insert, said insert being carried on said base, said insert having a face disposed toward said eye, said face having a surface portion according to a predetermined correction;

a knife, said knife being movable in said recess in a plane transverse to and adjacent said face;

a drive device for advancing said knife in said plane across said insert, said drive device being positioned and operable such that only said knife is movable across said insert;

said suction ring being couplable to a vacuum source, such that the application of vacuum to said vacuum chamber raises the inner ocular pressure of said eye causing the cornea of said eye to be urged into contact with said surface portion; and a knife motor coupled to said knife to move the cutting edge of said knife from side to side in an arc in said plane.

19. A device in accordance with claim 18 wherein:

said insert is removable; and wherein said base includes a portion for receiving said insert and retaining said insert in registered alignment with said base.

20. A surgical device in accordance with claim 19 wherein:

said insert is transparent.

21. A surgical device in accordance with claim 20 wherein:

said insert includes alignment markings thereon for aligning said device over an eye.

22. A surgical device in accordance with claim 18, wherein:

said knife motor includes a motor shaft, said motor being positioned such that said motor shaft is substantially perpendicular to said plane; and said surgical device further comprises an eccentric coupling said motor to said knife.

23. A surgical device in accordance with claim 22, wherein:

said eccentric comprises a bearing carried on said motor shaft.

24. A surgical device in accordance with claim 22, wherein:

said drive device comprises a linear actuator having an axially movable shaft coupled to said knife motor.

25. A surgical device in accordance with claim 18, wherein:

said base has a projection; and said insert includes a adapted to engage said projection whereby said insert will be carried on said base in a predetermined registered alignment.

26. An insert for use in a surgical device for altering the curvature of an eye, said device comprising a base portion, said base portion including a suction ring and a portion adapted to receive said insert, said suction ring cooperating with the eye to form a vacuum chamber, said device further comprising a knife edge movable by a drive device in a plane immediately below and adjacent said insert, said insert comprising:

a member having top and bottom faces, said bottom face having a surface portion shaped in accordance with a predetermined desired correction of said eye, said member having a groove adapted to engage a corresponding projection on said base whereby said insert will be carried on said base in a predetermined registered alignment.

27. An insert in accordance with claim 26 wherein:

said insert is formed of transparent material.

28. An insert in accordance with claim 26 wherein:

said material is an acrylic plastic.

29. An insert in accordance with claim 26 wherein:

said top face carries alignment markings and a scale thereon.

30. An insert in accordance with claim 26 wherein:

said surface portion is shaped such that a lenticular cut of desired refraction will be produced in a cornea of said eye by operation of said device.

31. An insert in accordance with claim 26 wherein:

said predetermined correction is an irregular correction of the cornea.

32. An insert in accordance with claim 26 wherein:

said predetermined correction comprises correction for astigmatism.

33. An insert in accordance with claim 26 wherein:

said predetermined correction corrects for myopia.

34. An insert in accordance with claim 26 wherein:

said predetermined correction corrects for hyperopia.

35. An insert in accordance with claim 26 wherein:

said surface portion is shaped such that a lenticular cut of desired refraction will be produced in a cornea of said eye by operation of said device.

36. An insert in accordance with claim 26 wherein:

said predetermined correction is an irregular correction of the cornea and said surface portion is shaped such the irregularities will be excised.

37. An insert in accordance with claim 26 wherein:

said surface portion is shaped such that a lamellar cut is produced.

38. An insert in accordance with claim 26 wherein:

said predetermined correction is a multifocal correction.

* * * * *